(12) United States Patent
Ito et al.

(10) Patent No.: US 10,912,341 B2
(45) Date of Patent: Feb. 9, 2021

(54) KNEE SUPPORTER AND GARMENT

(71) Applicant: MITSUI CHEMICALS, INC., Tokyo (JP)

(72) Inventors: Tomoaki Ito, Ichihara (JP); Aya Takeuchi, Ichihara (JP); Kenji Iida, Ichihara (JP); Motoyasu Yasui, Chiba (JP); Shiori Ito, Tsuchiura (JP); Kazuoki Nakai, Ichihara (JP); Fumihiko Kokido, Ichihara (JP); Fumiaki Saikawa, Kumamoto (JP)

(73) Assignee: MITSUI CHEMICALS, INC., Tokyo (JP)

( * ) Notice: Subject to any disclaimer, the term of this patent is extended or adjusted under 35 U.S.C. 154(b) by 67 days.

(21) Appl. No.: 16/071,990

(22) PCT Filed: Feb. 6, 2017

(86) PCT No.: PCT/JP2017/004286
§ 371 (c)(1),
(2) Date: Jul. 23, 2018

(87) PCT Pub. No.: WO2017/135473
PCT Pub. Date: Aug. 10, 2017

(65) Prior Publication Data
US 2019/0037937 A1    Feb. 7, 2019

(30) Foreign Application Priority Data

Feb. 4, 2016  (JP) .................................. 2016-020144
Dec. 5, 2016  (JP) .................................. 2016-236069

(51) Int. Cl.
*A41D 13/00* (2006.01)
*A41D 13/06* (2006.01)
(Continued)

(52) U.S. Cl.
CPC ............ *A41D 13/065* (2013.01); *A41D 13/06* (2013.01); *A61F 5/0109* (2013.01); *A61F 5/02* (2013.01)

(58) Field of Classification Search
CPC .. A41D 13/0543; A41D 13/06; A41D 13/065; A63B 71/1225; A61F 5/0106; A61F 5/0109; A61F 5/0123; A61F 5/02
(Continued)

(56) References Cited

U.S. PATENT DOCUMENTS 6,063,048 A * 5/2000 Bodenschatz ......... A61F 5/0109
                                                        2/22
6,592,539 B1 * 7/2003 Einarsson ............. A61F 5/0109
                                                        602/26
(Continued)

FOREIGN PATENT DOCUMENTS

JP   2000-116697 A   4/2000
JP   2003-052727 A   2/2003
(Continued)

OTHER PUBLICATIONS

Sep. 6, 2019 Extended Search Report issued in European Patent Application No. 17747623.1.
(Continued)

*Primary Examiner* — Richale L Quinn
(74) *Attorney, Agent, or Firm* — Oliff PLC

(57) ABSTRACT

A knee supporter, including a tubular supporter main body including: a knee anterior surface part; a knee posterior surface part; a femoral side anterior surface part; a femoral side posterior surface part; a tibial side anterior surface part; and a tibial side posterior surface part, wherein elastic moduli, in an axial direction of the tubular supporter main body, when stretched by 80% in the axial direction of the tubular supporter main body, satisfy the following Formula
(Continued)

(1) to (3): Formula (1): 0.7≤knee posterior surface part/knee anterior surface part; Formula (2): 1<femoral side anterior surface part/femoral side posterior surface part; and Formula (3): 1<tibial side anterior surface part/tibial side posterior surface part.

19 Claims, 3 Drawing Sheets

(51) Int. Cl.
    *A61F 5/02*     (2006.01)
    *A61F 5/01*     (2006.01)

(58) Field of Classification Search
    USPC .................................................. 2/22, 23, 24
    See application file for complete search history.

(56) References Cited

U.S. PATENT DOCUMENTS 7,975,634 B1 * 7/2011 Dugan ................. A41D 13/065
                                                            112/475.06
2014/0303534 A1 * 10/2014 Huffa ..................... A61F 5/0109
                                                             602/6
2015/0209170 A1 * 7/2015 Matsuo ................ A41D 13/065
                                                             602/26
2017/0238636 A1 * 8/2017 Einesson .......... A41D 19/01511

FOREIGN PATENT DOCUMENTS

| | | |
|---|---|---|
| JP | 2005-198897 A | 7/2005 |
| JP | 2007-009362 A | 1/2007 |
| JP | 2008-106404 A | 5/2008 |
| JP | 2010-013765 A | 1/2010 |
| JP | 2011-038230 A | 2/2011 |
| JP | 2011-130784 A | 7/2011 |
| JP | 2016-065326 A | 4/2016 |
| WO | 2011/090194 A1 | 7/2011 |

OTHER PUBLICATIONS

May 9, 2017 International Search Report issued in International Patent Application No. PCT/JP2017/004286.

* cited by examiner

KNEE SUPPORTER AND GARMENT

TECHNICAL FIELD

The present invention relates to a knee supporter and a garment.

BACKGROUND ART

Currently, various knee supporters are known.

For example, as a knee supporter which can be easily worn, can selectively compress, fix, keep warm, and so forth, an appropriate location in accordance with pain, and can be manufactured in a simple manufacturing process, a knee supporter, in which a plurality of regions having differing stretchability are formed by knitting differently at an area covering the patella periphery such that at least a part of the area is formed as a low stretch region having a lower stretchability compared to regions outside the area, is known (see, for example, Patent Document 1).

Further, as a supporter that can maintain a fitted state without slipping out of place even when extension and flexion of the knee are repeated, a knee supporter, in which the main component is formed of a stretchable material, the supporter main body is configured by members including a supporter anterior surface upper member, a supporter anterior surface lower member, and a supporter posterior surface member, the supporter anterior surface upper member includes a patella area, and, when expressing the longitudinal stretch rate of the supporter anterior surface upper member as A1, the lateral stretch rate thereof as B1, the longitudinal stretch rate of the supporter posterior surface member as A2, and the lateral stretch rate thereof as B2, A1>B1 and A2<B2 are satisfied, is known (see, for example, Patent Document 2).

Further, as a compression supporter for compressing the patellar ligament and holding the patella to favorably fix the knee joint, a compression supporter is known that is provided with a main body made of a stretchable material in a form that can be worn on the knee part, and with a low stretch region with a lower stretchability than the main body attached to the main body, so that the knee joint part and the surrounding muscle tendon are supported due to the difference in stretchability between the low stretch region and the main body, in which the low stretch region includes a front suspension region provided at a frontal part of the main body in a substantially U shape surrounding the lower part of the patella to compress the patellar ligament, and the low stretch region is composed of a low stretch material made of a resin fixed to the main body (see, for example, Patent Document 3).

Further, as a supporter for a knee joint which follows the movement of the skin around the knee joint, is not easily displaced, and is easily put on, a supporter for a knee joint, which is formed in a sleeve shape up to 10 cm above and below the center of the knee joint of the main body, and in which the anterior surface part of the main body is configured by a highly stretchable material with a low modulus in the longitudinal direction, a notch is provided at least in the upper part of the anterior surface of the main body at 10 cm or more from the center of the knee joint, and, further, a member capable of adjusting the compressive force in the circumferential direction of the main body is provided across the notch, is known (see, for example, Patent Document 4).

Further, as a knee supporter which has an appropriate compressing property at the time of wearing, but does not tighten the knee excessively to cause pain, and allows the knee to bend and stretch satisfactorily, a supporter for the knee joint, which is provided with tightening parts at the upper and lower positions for preventing sliding down, a kneecap part, an X-shaped part extending diagonally, and other knitted fabric parts, in which the kneecap part is made of a knitted fabric having the lowest compression force at the time of wearing, the X-shaped part extending diagonally is made of a compressive knitted fabric, and the other knitted fabric parts are made of a buffering knitted fabric enabling the knee joint to bend and stretch easily, is known (see, for example, Patent Document 5).

Patent Document 1: Japanese Patent Application Laid-Open (JP-A) No. 2011-130784
Patent Document 2: JP-A No. 2007-9362
Patent Document 3: JP-A No. 2010-13765
Patent Document 4: JP-A No. 2000-116697
Patent Document 5: JP-A No. 2007-54126

SUMMARY OF INVENTION

Technical Problem

Improvement of the sense of fixation of a knee supporter to the knee joint is desired.

However, as a result of studies made by the present inventors, it has been found that when a knee supporter having a tubular supporter main body is improved in terms of the sense of fixation to the knee joint, it may become difficult to perform bending and stretching movements of the knee joint.

The easiness of bending and stretching movements of a knee joint is herein referred to as "ease of bending and stretching movements of the knee joint".

An object of an embodiment of the invention is to provide a knee supporter which is superior in a sense of fixation to the knee joint and ease of bending and stretching movements of the knee joint.

An object of another embodiment of the invention is to provide a garment including a knee supporter which is superior in a sense of fixation to the knee joint and ease of bending and stretching movements of the knee joint.

An object of a further other embodiment of the invention is to provide a garment including a joint supporter unit which is superior in a sense of fixation to a joint, and suppresses dislocation at the time of wearing.

Solution to Problem

Specific means for solving the above problem include the following embodiments.

<1> A knee supporter, comprising a tubular supporter main body that is worn on a part of a leg including a knee, the tubular supporter main body comprising:

a knee anterior surface part (A) that supports an anterior surface of the knee;

a knee posterior surface part (B) that supports a posterior surface of the knee;

a femoral side anterior surface part (C) that supports an anterior surface of a femoral side, with respect to the knee, of the leg;

a femoral side posterior surface part (D) that supports a posterior surface of the femoral side;

a tibial side anterior surface part (E) that supports an anterior surface of a tibial side, with respect to the knee, of the leg; and a tibial side posterior surface part (F) that supports a posterior surface of the tibial side, wherein elastic moduli, in an axial direction of the tubular supporter main body, of the knee anterior surface part (A), the knee posterior surface part (B), the femoral side anterior surface part (C), the femoral side posterior surface part (D), the tibial side anterior surface part (E), and the tibial side posterior surface part (F), when stretched by 80% in the axial direction of the tubular supporter main body, satisfy the following Formulae (1) to (3):

$$0.7 \leq \text{knee posterior surface part}(B)/\text{knee anterior surface part}(A); \quad \text{Formula (1):}$$

$$1 < \text{femoral side anterior surface part}(C)/\text{femoral side posterior surface part}(D); \text{ and} \quad \text{Formula (2):}$$

$$1 < \text{tibial side anterior surface part}(E)/\text{tibial side posterior surface part}(F). \quad \text{Formula (3):}$$

<2> The knee supporter according to <1>, wherein the elastic moduli in the axial direction of the knee anterior surface part (A), the femoral side anterior surface part (C), and the tibial side anterior surface part (E), when stretched by 80% in the axial direction of the tubular supporter main body, satisfy at least one of the following Formula (4X) or (5X):

$$1 < \text{knee anterior surface part}(A)/\text{femoral side anterior surface part }(C); \text{ and} \quad \text{Formula (4X):}$$

$$1 < \text{knee anterior surface part}(A)/\text{tibial side anterior surface part}(E). \quad \text{Formula (5X):}$$

<3> The knee supporter according to <2>, wherein the elastic moduli in the axial direction of the knee anterior surface part (A), the femoral side anterior surface part (C), and the tibial side anterior surface part (E), when stretched by 80% in the axial direction of the tubular supporter main body, satisfy both Formulae (4X) and (5X).

<4> The knee supporter according to any one of <1> to <3>, wherein the elastic moduli in the axial direction of the knee anterior surface part (A), the femoral side anterior surface part (C), and the tibial side anterior surface part (E), when stretched by 80% in the axial direction of the tubular supporter main body, satisfy at least one of the following Formula (4Xa) or (5Xa):

$$1 < \text{knee anterior surface part}(A)/\text{femoral side anterior surface part }(C) \leq 5; \text{ and} \quad \text{Formula (4Xa):}$$

$$1 < \text{knee anterior surface part}(A)/\text{tibial side anterior surface part }(E) \leq 5. \quad \text{Formula (5Xa):}$$

<5> The knee supporter according to <1>, wherein the elastic moduli in the axial direction of the knee anterior surface part (A), the femoral side anterior surface part (C), and the tibial side anterior surface part (E), when stretched by 80% in the axial direction of the tubular supporter main body, satisfy at least one of the following Formula (4Y) or (5Y):

$$0.2 \leq \text{knee anterior surface part}(A)/\text{femoral side anterior surface part }(C) \leq 1; \text{ and} \quad \text{Formula (4Y):}$$

$$0.2 \leq \text{knee anterior surface part}(A)/\text{tibial side anterior surface part }(E) \leq 1. \quad \text{Formula (5Y):}$$

<6> The knee supporter according to <5>, wherein the elastic moduli in the axial direction of the knee anterior surface part (A), the femoral side anterior surface part (C), and the tibial side anterior surface part (E), when stretched by 80% in the axial direction of the tubular supporter main body, satisfy both Formulae (4Y) and (5Y).

<7> The knee supporter according to any one of <1> to <6>, wherein the elastic moduli in the axial direction of the femoral side anterior surface part (C), the femoral side posterior surface part (D), the tibial side anterior surface part (E), and the tibial side posterior surface part (F), when stretched by 80% in the axial direction of the tubular supporter main body, satisfy at least one of the following Formula (6) or (7):

$$1 < \text{tibial side anterior surface part}(E)/\text{femoral side posterior surface part}(D); \text{ and} \quad \text{Formula (6):}$$

$$1 < \text{femoral side anterior surface part}(C)/\text{tibial side posterior surface part}(F). \quad \text{Formula (7):}$$

<8> The knee supporter according to any one of <1> to <7>, wherein the elastic moduli in the axial direction of the knee posterior surface part (B), the femoral side posterior surface part (D), and the tibial side posterior surface part (F), when stretched by 80% in the axial direction of the tubular supporter main body, satisfy at least one of the following Formula (8) or (9):

$$6 \leq \text{knee posterior surface part}(B)/\text{femoral side posterior surface part }(D) \leq 50; \text{ and} \quad \text{Formula (8):}$$

$$6 \leq \text{knee posterior surface part}(B)/\text{tibial side posterior surface part}(F) \leq 50. \quad \text{Formula (9):}$$

<9> The knee supporter according to any one of <1> to <8>, wherein the elastic moduli in the axial direction of the femoral side anterior surface part (C), the femoral side posterior surface part (D), the tibial side anterior surface part (E), and the tibial side posterior surface part (F), when stretched by 80% in the axial direction of the tubular supporter main body, satisfy at least one of the following Formula (2a) or (3a):

$$2 \leq \text{femoral side anterior surface part}(C)/\text{femoral side posterior surface part}(D) \leq 40; \text{ and} \quad \text{Formula (2a):}$$

$$2 \leq \text{tibial side anterior surface part}(E)/\text{tibial side posterior surface part}(F) \leq 40. \quad \text{Formula (3a):}$$

<10> The knee supporter according to any one of <1> to <9>, wherein the elastic moduli in the axial direction of the knee anterior surface part (A) and the knee posterior surface part (B), when stretched by 80% in the axial direction of the tubular supporter main body, satisfy the following Formula (1a):

$$0.7 \leq \text{knee posterior surface part}(B)/\text{knee anterior surface part}(A) \leq 3. \quad \text{Formula (1a):}$$

<11> The knee supporter according to any one of <1> to <10>, wherein the elastic modulus in the axial direction of each of the femoral side posterior surface part (D) and the tibial side posterior surface part (F), when stretched by 80% in the axial direction of the tubular supporter main body, is 0.001 MPa or more, and the elastic modulus in the axial direction of the knee posterior surface part (B), when stretched by 80% in the axial direction of the tubular supporter main body, is 1.0 MPa or less.

<12> The knee supporter according to any one of <1> to <11>, wherein each of a knit structure of the knee anterior surface part (A), a knit structure of the knee posterior surface part (B), a knit structure of the femoral side anterior surface part (C), a knit structure of the femoral side posterior surface part (D), a knit structure of the tibial side anterior surface part (E), and a knit structure of the tibial side posterior surface part (F), includes a float stitch structure.

<13> The knee supporter according to any one of <1> to <12>, wherein a stretch rate in the axial direction of the knee anterior surface part (A), when stretched in the axial direction of the tubular supporter main body at a load of 20 N, is from 50% to 500%.

<14> The knee supporter according to any one of <1> to <13>, wherein a stretch rate in the axial direction of each of the femoral side posterior surface part (D) and the tibial side posterior surface part (F), when stretched in the axial direction of the tubular supporter main body at a load of 20 N, is from 150% to 850%.

<15> The knee supporter according to any one of <1> to <14>, wherein the tubular supporter main body is continuously manufactured by circular knitting.

<16> The knee supporter according to any one of <1> to <15>, wherein the tubular supporter main body has a seamless structure.

<17> The knee supporter according to any one of <1> to <16>, further comprising a femoral side rib top part disposed on a femoral side of the tubular supporter main body, and a tibial side rib top part disposed on a tibial side of the tubular supporter main body.

<18> The knee supporter according to any one of <1> to <17>, wherein the knee posterior surface part (B)/the knee anterior surface part (A) in Formula (1) is more than 1.

<19> The knee supporter according to any one of <1> to <18>, wherein the knee posterior surface part (B)/the knee anterior surface part (A) in Formula (1) is 1.1 or higher.

<20> A garment, comprising the knee supporter according to any one of <1> to <19>.

<21> A garment, comprising a tubular joint supporter unit, the tubular joint supporter unit comprising:

a central region in an axial direction of the tubular joint supporter unit, which supports a joint part of a wearer's body;

a one-end side region located at one end side in the axial direction with respect to the central region; and an other-end side region located at another end side in the axial direction with respect to the central region, wherein, in a case in which an elastic modulus in the axial direction when a region is stretched by 80% in the axial direction is defined as an 80% axial direction elastic modulus, a minimum value of the 80% axial direction elastic modulus in the central region is defined as an elastic modulus EC, a minimum value of the 80% axial direction elastic modulus in the one-end side region is defined as an elastic modulus EE1, and a minimum value of the 80% axial direction elastic modulus in the other-end side region is defined as an elastic modulus EE2, the elastic modulus EC is 5 to 50 times as high as at least one of the elastic modulus EE1 or the elastic modulus EE2.

<22> The garment according to <21>, wherein, in a case in which, in the tubular joint supporter unit, a semicircular side including an outer side when a joint is bent is defined as an anterior surface part, and a semicircular side including an inner side when a joint is bent is defined as a posterior surface part, a region exhibiting the elastic modulus EE1 is positioned in the posterior surface part in the one-end side region, and a region exhibiting the elastic modulus EE2 is positioned in the posterior surface part in the other-end side region.

<23> The garment according to <21> or <22>, wherein each of the region exhibiting the elastic modulus EE1 and the region exhibiting the elastic modulus EE2 includes a concave-convex structure region.

<24> The garment according to <23>, wherein the concave-convex structure region is a concave-convex knitted fabric region comprising a repeated tuck stitch structure.

<25> The garment according to any one of <21> to <24>, wherein each of the elastic modulus EE1 and the elastic modulus EE2 is 0.001 MPa or more.

<26> The garment according to any one of <21> to <25>, wherein the central region is worn on a knee joint, an elbow joint, a wrist joint, a finger joint, or a toe joint.

<27> The garment according to any one of <21> to <26>, wherein the central region is worn on a knee joint.

Advantageous Effects of Invention

According to an embodiment of the invention, a knee supporter which is superior in a sense of fixation to the knee joint and ease of bending and stretching movements of the knee joint is provided.

According to another embodiment of the invention, a garment including a knee supporter which is superior in a sense of fixation to the knee joint and ease of bending and stretching movements of the knee joint is provided.

According to a further other embodiment of the invention, a garment including a joint supporter unit which is superior in a sense of fixation to a joint, and suppresses dislocation at the time of wearing is provided.

DESCRIPTION OF EMBODIMENTS

Figure 1:
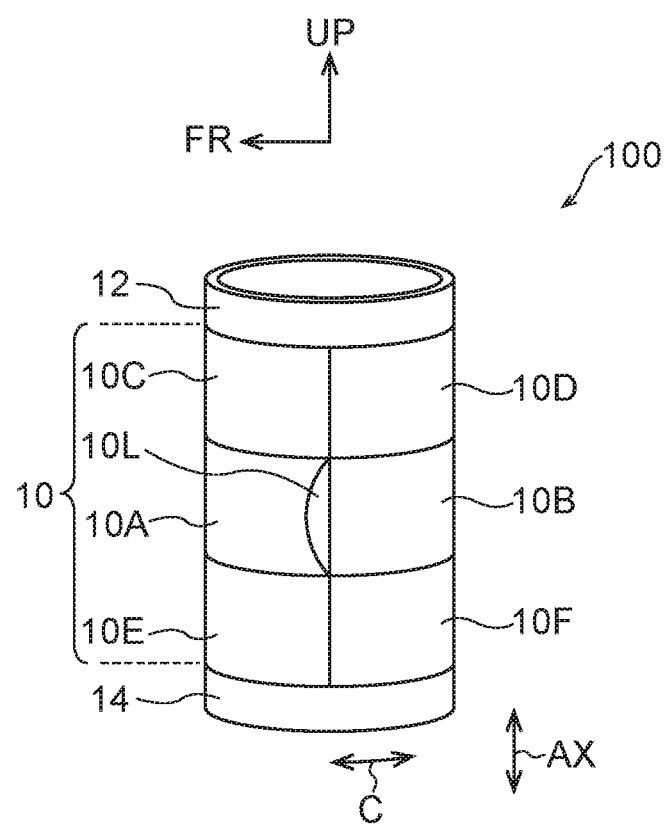
FIG. 1 is a schematic perspective view of a knee supporter according to a specific example of the invention.

An embodiment of the invention (hereinafter also referred to as "embodiment") will be described below.

A numerical range expressed by "x to y" herein includes the values of x and y in the range as the minimum and maximum values, respectively.

Further, the term "axial direction of a tubular supporter main body" means herein the axial direction of the tubular shape when the shape of a tubular supporter main body is maintained in a tubular shape. The "axial direction of a tubular supporter main body" may be herein simply referred to as "axial direction". The "axial direction" herein means a direction sometimes referred to as "longitudinal direction" in the technical field concerning a knee supporter, which may be also expressed as a direction, along which a leg is inserted into a tubular supporter main body.

Meanwhile, the "circumferential direction of a tubular supporter main body" means herein the circumferential direction when the shape of a tubular supporter main body is maintained in a tubular shape. The "circumferential direction of a tubular supporter main body" may be herein simply referred to as "circumferential direction". The "circumferential direction" herein means a direction sometimes referred to as "lateral direction" in the technical field concerning a knee supporter.

Further, herein, the side of the patella of the leg is called "anterior surface" and the side of the back of the knee is called "posterior surface".

[Knee Supporter]

A knee supporter of the embodiment is a knee supporter, comprising a tubular supporter main body that is worn on a part of a leg including a knee, the tubular supporter main body comprising:

a knee anterior surface part (A) that supports an anterior surface of the knee;

a knee posterior surface part (B) that supports a posterior surface of the knee;

a femoral side anterior surface part (C) that supports an anterior surface of a femoral side, with respect to the knee, of the leg;

a femoral side posterior surface part (D) that supports a posterior surface of the femoral side;

a tibial side anterior surface part (E) that supports an anterior surface of a tibial side, with respect to the knee, of the leg; and a tibial side posterior surface part (F) that supports a posterior surface of the tibial side, wherein elastic moduli, in an axial direction of the tubular supporter main body, of the knee anterior surface part (A), the knee posterior surface part (B), the femoral side anterior surface part (C), the femoral side posterior surface part (D), the tibial side anterior surface part (E), and the tibial side posterior surface part (F), when stretched by 80% in the axial direction of the tubular supporter main body, (hereinafter also referred to as "80% axial direction elastic moduli") satisfy the following Formulae (1) to (3):

$$0.7 \leq \text{knee posterior surface part}(B)/\text{knee anterior surface part}(A); \quad \text{Formula (1):}$$

$$1 < \text{femoral side anterior surface part}(C)/\text{femoral side posterior surface part}(D); \text{ and} \quad \text{Formula (2):}$$

$$1 < \text{tibial side anterior surface part}(E)/\text{tibial side posterior surface part }(F). \quad \text{Formula (3):}$$

When a knee supporter of the embodiment is configured as above, it may be superior in sense of fixation to the knee joint and ease of bending and stretching movements of the knee joint.

The aforedescribed effects (sense of fixation to the knee joint, and ease of bending and stretching movements of the knee joint) will be described in more detail below.

Through the investigation by the inventors, it has been found that there is a positive correlation between the elastic modulus of a knee supporter and the sense of fixation to the leg of the knee supporter. That is, it has become clear that as the elastic modulus of a knee supporter increases, the compression applied to the leg at the time of wearing may be increased all the more (namely, the tightening force against the leg can be strengthened), and as a result, the sense of fixation to the leg may be improved as the bodily sensation of a wearer.

Further, it has been known through the investigation by the inventors that the sense of fixation to the knee joint may be improved effectively when the 80% axial direction elastic modulus of the knee posterior surface part (B) is 0.7 times or more as high as the 80% axial direction elastic modulus of the knee anterior surface part (A) (namely when Formula (1) is satisfied).

On the other hand, there is a negative correlation between the elastic modulus of the knee supporter and the elongation of the knee supporter.

In this regard, in the case of the knee supporter of the embodiment, when the 80% axial direction elastic modulus of the femoral side posterior surface part (D) is lower than the 80% axial direction elastic modulus of the femoral side anterior surface part (C), and the 80% axial direction elastic modulus of the tibial side posterior surface part (F) is lower than the 80% axial direction elastic modulus of the tibial side anterior surface part (E) (namely when Formulae (2) and (3) are satisfied), elongation of the femoral side posterior surface part (D) and the tibial side posterior surface part (F) in a state where the knee joint is bent is secured, and therefore the ease of bending and stretching movements of the knee joint is improved. More particularly, the femoral side posterior surface and the tibial side posterior surface of the leg are surfaces having a body fat percentage higher than the femoral side anterior surface and the tibial side anterior surface of the leg, and located inside when the knee joint is bent. Therefore, the femoral side posterior surface part (D) and the tibial side posterior surface part (F) are required to stretch in a bending motion of the knee joint. Therefore, in the embodiment, the 80% axial direction elastic moduli of the femoral side posterior surface part (D) and the tibial side posterior surface part (F) are made lower than the 80% axial direction elastic moduli of the femoral side anterior surface part (C) and the tibial side anterior surface part (E), respectively, so that elongation of the femoral side posterior surface part (D) and the tibial side posterior surface part (F) in association with bending of the knee is secured, and consequently the ease of bending and stretching movements of the knee joint is improved.

The 80% axial direction elastic modulus of the knee anterior surface part (A) means herein a value measured for a range, which has the measurement center at the central position of the knee anterior surface part (A) (namely, a position that is the center in the circumferential direction, and also the center in the axial direction), and has a measurement width (namely, length in the circumferential direction) of 15 mm.

The same holds for the respective 80% axial direction elastic moduli of the knee posterior surface part (B), the femoral side anterior surface part (C), the femoral side posterior surface part (D), the tibial side anterior surface part (E), and the tibial side posterior surface part (F).

An "80% axial direction elastic modulus" is measured herein by a tensile test under conditions of a grip width of 15 mm, a grip distance of 15 mm, and a tensile load of 20 N. In this regard, the direction of the tensile load is the axial direction of a supporter main body.

In the tensile test for measuring an 80% axial direction elastic modulus, a part of the knee supporter is fixed to a tensile tester with a grip width of 15 mm and a grip distance of 15 mm, and stretched at a tensile speed of 15 mm/min and the elastic modulus at 80% elongation is read out as the measured value.

Further, in a case where it is difficult to perform the tensile test on a part of a knee supporter, a test piece of 30 mm square may be cut out from the knee supporter and the test may be performed on the cut out test piece.

The number of tests is five, the average value is calculated from three measurement values excluding the maximum value and the minimum value from the five measurement values, and this average value is adopted as an "80% axial direction elastic modulus".

A general tensile tester may be used as an apparatus for the tensile test, and for example, an Autograph "AGS-X 1kN" manufactured by Shimadzu Corporation may be used.

Knee posterior surface part (B)/knee anterior surface part (A) in Formula (1) is 0.7 or higher as written in Formula (1). The knee posterior surface part (B)/knee anterior surface part (A) in Formula (1) is preferably 0.8 or higher from the viewpoint of improvement of sense of fixation to the knee joint, more preferably 1 or higher, further preferably higher than 1, and especially preferably 1.1 or higher.

In the knee supporter of the embodiment, the elastic moduli in the axial direction of the knee anterior surface part (A) and the knee posterior surface part (B), when stretched by 80% in the axial direction of the tubular supporter main body, preferably satisfy the following Formula (1a).

$$0.7 \leq \text{knee posterior surface part}(B)/\text{knee anterior surface part}(A) \leq 3 \quad \text{Formula (1a)}$$

The left side of Formula (1a) (0.7≤knee posterior surface part (B)/knee anterior surface part (A)) has the same meaning as Formula (1), and its effect (sense of fixation to the knee joint) and the preferable lower limit value of knee posterior surface part (B)/knee anterior surface part (A) are also the same.

The sense of fixation to the knee joint is further improved by satisfying the right side of Formula (1a) (knee posterior surface part (B)/knee anterior surface part (A)≤3).

The knee posterior surface part (B)/knee anterior surface part (A) in Formula (1a) is preferably 2 or less, and more preferably 1.5 or less.

The 80% axial direction elastic moduli of the femoral side anterior surface part (C), the femoral side posterior surface part (D), the tibial side anterior surface part (E), and the tibial side posterior surface part (F) in the knee supporter of the embodiment preferably satisfy at least one of the following Formula (2a) or Formula (3a) (preferably the following Formula (3a), more preferably both the following Formula (2a) and Formula (3a)).

$$2 \leq \text{femoral side anterior surface part}(C)/\text{femoral side posterior surface part}(D) \leq 40 \quad \text{Formula (2a)}$$

$$2 \leq \text{tibial side anterior surface part}(E)/\text{tibial side posterior surface part}(F) \leq 40 \quad \text{Formula (3a)}$$

When the knee supporter of the embodiment satisfies at least one of the left side of Formula (2a) (2≤femoral side anterior surface part (C)/femoral side posterior surface part (D)) or the left side of Formula (3a) (2≤tibial side anterior surface part (E)/tibial side posterior surface part (F)), the ease of bending and stretching movements of the knee joint is improved.

When the knee supporter of the embodiment satisfies at least one of the right side of Formula (2a) (femoral side anterior surface part (C)/femoral side posterior surface part (D)≤40) or the right side of Formula (3a) (tibial side anterior surface part (E)/tibial side posterior surface part (F)≤40), dislocation of the femoral side posterior surface part (D) and the tibial side posterior surface part (F) may be further suppressed.

The femoral side anterior surface part (C)/femoral side posterior surface part (D) in Formula (2a) is preferably 30 or less, and more preferably 20 or less.

The tibial side anterior surface part (E)/tibial side posterior surface part (F) in Formula (3a) is preferably 30 or less, and more preferably 20 or less.

As a preferable mode (hereinafter also referred to as "first mode") of a knee supporter according to the embodiment, there is a mode, in which the elastic moduli in the axial direction of the knee anterior surface part (A), the femoral side anterior surface part (C), and the tibial side anterior surface part (E), when stretched by 80% in the axial direction of the tubular supporter main body, satisfy at least one of the following Formula (4X) or (5X) (preferably the following Formula (5X), more preferably both the following Formula (4X) and Formula (5X)).

$$1 < \text{knee anterior surface part}(A)/\text{femoral side anterior surface part}(C) \quad \text{Formula (4X)}$$

$$1 < \text{knee anterior surface part}(A)/\text{tibial side anterior surface part}(E) \quad \text{Formula (5X)}$$

The first mode is a mode, in which the 80% axial direction elastic modulus of the knee anterior surface part (A) is relatively higher than the 80% axial direction elastic modulus of at least one (preferably both) of the femoral side anterior surface part (C) and the tibial side anterior surface part (E).

By the first mode, the sense of fixation to the knee joint is more effectively improved according to a bodily sensation of a wearer. In other words, the first mode is particularly suitable for a case where the sense of fixation to the knee joint is emphasized.

In the knee supporter of the first mode, when a knee anterior surface part (A), a knee posterior surface part (B), a femoral side anterior surface part (C), and a femoral side posterior surface part (D) are arranged in the descending order of the 80% axial direction elastic moduli, a preferable order is: one of the knee anterior surface part (A) and the knee posterior surface part (B), the other one of the knee anterior surface part (A) and the knee posterior surface part (B), the femoral side anterior surface part (C), and the femoral side posterior surface part (D).

Further, in the knee supporter of the first mode, when a knee anterior surface part (A), a knee posterior surface part (B), a tibial side anterior surface part (E), and a tibial side posterior surface part (F) are arranged in the descending order of the 80% axial direction elastic moduli, a preferable order is: one of the knee anterior surface part (A) and the knee posterior surface part (B), the other one of the knee anterior surface part (A) and the knee posterior surface part (B), the tibial side anterior surface part (E), and the tibial side posterior surface part (F).

The 80% axial direction elastic moduli of a knee anterior surface part (A), a femoral side anterior surface part (C), and a tibial side anterior surface part (E) of the first mode preferably satisfy at least one of the following Formula (4Xa) or Formula (5Xa) (preferably the following Formula (5Xa), more preferably both the following Formula (4Xa) and Formula (5Xa)).

$$1 \leq \text{knee anterior surface part}(A)/\text{femoral side anterior surface part}(C) \leq 5 \quad \text{Formula (4Xa)}$$

$$1 \leq \text{knee anterior surface part}(A)/\text{tibial side anterior surface part}(E) \leq 5 \quad \text{Formula (5Xa)}$$

When the knee supporter of the first mode satisfies at least one of the left side of Formula (4Xa) (1<knee anterior surface part (A)/femoral side anterior surface part (C)) or the left side of Formula (5Xa) (1<knee anterior surface part (A)/tibial side anterior surface part (E)), the sense of fixation to the knee joint is improved.

In the first mode, the knee anterior surface part (A)/femoral side anterior surface part (C) is preferably 1.5 or more from the viewpoint of improvement of sense of fixation to the knee joint, and more preferably 2 or more.

In the first mode, the knee anterior surface part (A)/tibial side anterior surface part (E) is preferably 1.5 or more from the viewpoint of improvement of sense of fixation to the knee joint, and more preferably 2 or more.

When the knee supporter of the first mode satisfies at least one of the right side of Formula (4Xa) (knee anterior surface part (A)/femoral side anterior surface part (C)≤5) or the right side of Formula (5Xa) (knee anterior surface part (A)/tibial side anterior surface part (E)≤5), excessive tightening (compression) against the knee may be suppressed.

As a preferable mode other than the first mode (hereinafter also referred to as "second mode") of a knee supporter according to the embodiment, there is also a mode, in which the elastic moduli in the axial direction of the knee anterior surface part (A), the femoral side anterior surface part (C), and the tibial side anterior surface part (E), when stretched by 80% in the axial direction of the tubular supporter main body, satisfy at least one of the following Formula (4Y) or (5Y) (preferably the following Formula (5Y), more preferably both the following Formula (4Y) and Formula (5Y)).

$$0.2 \leq \text{knee anterior surface part}(A)/\text{femoral side anterior surface part}(C) \leq 1 \quad \text{Formula (4Y)}$$

$$0.2 \leq \text{knee anterior surface part}(A)/\text{tibial side anterior surface part}(E) \leq 1 \quad \text{Formula (5Y)}$$

The second mode is a mode, in which the 80% axial direction elastic modulus of the knee anterior surface part (A) is relatively not higher than the 80% axial direction elastic modulus of at least one (preferably both) of the femoral side anterior surface part (C) and the tibial side anterior surface part (E).

By the second mode, the ease of bending and stretching movements of the knee joint is more effectively improved according to a bodily sensation of a wearer. In other words, the second mode is particularly suitable for a case where the ease of bending and stretching movements of the knee joint is emphasized.

As a preferable mode other than the first mode and the second mode (hereinafter also referred to as "third mode") of a knee supporter according to the embodiment, there is a mode, in which the elastic moduli in the axial direction of the knee anterior surface part (A), the femoral side anterior surface part (C), and the tibial side anterior surface part (E), when stretched by 80% in the axial direction of the tubular supporter main body, satisfy Formula (4X) in the first mode and Formula (5Y) in the second mode.

In the third mode, the elastic moduli in the axial direction satisfy femoral side anterior surface part (C)<knee anterior surface part (A) tibial side anterior surface part (E).

By the third mode, the ease of bending and stretching movements of the knee joint is more effectively improved according to a bodily sensation of a wearer. In other words, the third mode is particularly suitable for a case where the ease of bending and stretching movements of the knee joint is emphasized.

The 80% axial direction elastic moduli of the femoral side anterior surface part (C), the femoral side posterior surface part (D), the tibial side anterior surface part (E), and the tibial side posterior surface part (F) in the knee supporter of the embodiment (including the knee supporters of the first to third modes, the same shall apply hereinafter), preferably satisfy at least one of the following Formula (6) or Formula (7).

In this way, the ease of bending and stretching movements of the knee joint is further improved.

$$1 < \text{tibial side anterior surface part}(E)/\text{femoral side posterior surface part}(D) \quad \text{Formula (6)}$$

$$1 < \text{femoral side anterior surface part}(C)/\text{tibial side posterior surface part}(F) \quad \text{Formula (7)}$$

Tibial side anterior surface part (E)/femoral side posterior surface part (D) in Formula (6) is preferably 40 or less.

Femoral side anterior surface part (C)/tibial side posterior surface part (F) in Formula (7) is preferably 40 or less.

The 80% axial direction elastic moduli of the knee posterior surface part (B), the femoral side posterior surface part (D), and the tibial side posterior surface part (F) in the knee supporter of the embodiment preferably satisfy at least one of the following Formula (8) or Formula (9) (preferably the following Formula (9), more preferably both the following Formula (8) and Formula (9)).

$$6 \leq \text{knee posterior surface part}(B)/\text{femoral side posterior surface part}(D) \leq 50 \quad \text{Formula (8)}$$

$$6 \leq \text{knee posterior surface part}(B)/\text{tibial side posterior surface part}(F) \leq 50 \quad \text{Formula (9)}$$

When the knee supporter of the embodiment satisfies at least one of the left side of Formula (8) (6≤knee posterior surface part (B)/femoral side posterior surface part (D)) or the left side of Formula (9) (6≤knee posterior surface part (B)/tibial side posterior surface part (F)), the sense of fixation to the knee joint is improved.

When the knee supporter of the embodiment satisfies at least one of the right side of Formula (8) (knee posterior surface part (B)/femoral side posterior surface part (D)≤50) or the right side of Formula (9) (knee posterior surface part (B)/tibial side posterior surface part (F)≤50), dislocation of at least one of the femoral side posterior surface part (D) or the tibial side posterior surface part (F) (dislocation at the time of wearing, the same shall apply hereinafter) is further suppressed.

In Formula (8), the knee posterior surface part (B)/femoral side posterior surface part (D) is preferably 10 or more.

In Formula (9), the knee posterior surface part (B)/tibial side posterior surface part (F) is preferably 10 or more.

In the knee supporter of the embodiment, the 80% axial direction elastic modulus of the femoral side posterior surface part (D) is preferably 0.001 MPa or more from the viewpoint of better suppression of dislocation of the femoral side posterior surface part (D), and more preferably 0.01 MPa or more.

Also, in the knee supporter of the embodiment, the 80% axial direction elastic modulus of the femoral side posterior surface part (D) is preferably 0.1 MPa or less, and more preferably 0.08 MPa or less.

From the viewpoint of suppressing dislocation of the tibial side posterior surface part (F) in the knee supporter of the embodiment, the 80% axial direction elastic modulus of the tibial side posterior surface part (F) is preferably 0.001 MPa or more, and more preferably 0.01 MPa or more.

Also, the 80% axial direction elastic modulus of the tibial side posterior surface part (F) in the knee supporter of the embodiment is preferably 0.1 MPa or less, and more preferably 0.08 MPa or less.

Also, from the viewpoint of suppressing excessive tightening (compression) against the knee and improving comfort in wearing the knee supporter of the embodiment, the 80% axial direction elastic modulus of the knee posterior surface part (B) is preferably 1.0 MPa or less, and more preferably 0.7 MPa or less.

Also, from the viewpoint of improving the sense of fixation to the knee for the knee supporter of the embodiment, the 80% axial direction elastic modulus of the knee posterior surface part (B) is preferably 0.05 MPa or more, and more preferably 0.3 MPa or more.

From the viewpoint of suppressing dislocation of the femoral side anterior surface part (C) in the knee supporter of the embodiment, the 80% axial direction elastic modulus of the femoral side anterior surface part (C) is preferably 0.001 MPa or more, and more preferably 0.5 MPa or more.

Also, in the knee supporter of the embodiment, the 80% axial direction elastic modulus of the femoral side anterior surface part (C) is preferably 1.9 MPa or less, and more preferably 1.2 MPa or less.

In the knee supporter of the embodiment, from the viewpoint of suppressing dislocation of the tibial side anterior surface part (E), the 80% axial direction elastic modulus of the tibial side anterior surface part (E) is preferably 0.001 MPa or more, and more preferably 0.5 MPa or more.

Also, in the knee supporter of the embodiment, the 80% axial direction elastic modulus of the tibial side anterior surface part (E) is preferably 1.9 MPa or less, and more preferably 1.2 MPa or less.

Also, from the viewpoints of suppressing excessive tightening (compression) against the knee and improving comfort in wearing the knee supporter of the embodiment, the 80% axial direction elastic modulus of the knee anterior surface part (A) is preferably 0.8 MPa or less, and more preferably 0.6 MPa or less.

Also, from the viewpoint of improving the sense of fixation to the knee in the knee supporter of the embodiment, the 80% axial direction elastic modulus of the knee anterior surface part (A) is preferably 0.1 MPa or more, and more preferably 0.3 MPa or more.

In the knee supporter of the embodiment, each of the knit structure of the knee anterior surface part (A), the knit structure of the knee posterior surface part (B), the knit structures of the femoral side anterior surface part (C), the knit structure of the femoral side posterior surface part (D), the knit structure of the tibial side anterior surface part (E), and the knit structure of the tibial side posterior surface part (F) is preferably a knit structure including a float stitch structure.

In a case in which the knit structure of each of the above parts is a knit structure including a float stitch structure, the axial direction elastic modulus of each part may be easily adjusted by changing the density and distribution of float yarns in each part during production of the knee supporter. By doing so, a knee supporter satisfying Formulae (1) to (3) may be easily produced.

Further, in the knee supporter of the embodiment, each of the femoral side posterior surface part (D) and the tibial side posterior surface part (F) preferably has a concave-convex structure region. In such a mode, especially at least one of the Formula (8) or Formula (9) may be achieved easily.

With respect to a preferable form of a concave-convex structure region, the preferable form of a concave-convex structure region in a garment of the mode B described below may be referred to.

The stretch rate in the axial direction of the knee anterior surface part (A), when stretched in the axial direction of the tubular supporter main body at a load of 20 N (hereinafter also referred to simply as "20 N axial direction stretch rate"), is preferably from 50% to 500%.

When the 20 N axial direction stretch rate of the knee anterior surface part (A) is 50% or more, the ease of bending and stretching movements of the knee joint is improved.

When the 20 N axial direction stretch rate of the knee anterior surface part (A) is 500% or less, the sense of fixation to the knee joint is improved.

The 20 N axial direction stretch rate of the knee anterior surface part (A) is preferably 400% or less from the viewpoint of improvement of the sense of fixation to the knee joint, more preferably 300% or less, and especially preferably 200% or less.

The 20 N axial direction stretch rate of the knee anterior surface part (A) means herein a value measured for a range, which has the measurement center at the central position of the knee anterior surface part (A) (namely, a position that is the center in the circumferential direction, and also the center in the axial direction), and has a measurement width (namely, length in the circumferential direction) of 15 mm.

The same holds for the 20 N axial direction stretch rate of the femoral side posterior surface part (D) and the 20 N axial direction stretch rate of the tibial side support part described later.

A "20 N axial direction stretch rate" is measured herein by a tensile test under conditions of a grip width of 15 mm, a grip distance of 15 mm, and a tensile load of 20 N. In this regard, the direction of the tensile load is the axial direction of a supporter main body.

The "20 N axial direction stretch rate" refers to a value calculated by the following Formula 1.

$$20 \text{ N axial direction stretch rate } (\%) = (L_{20}/L_0) \times 100 \quad \text{Formula 1}$$

[In Formula 1, $L_0$ represents the initial grip distance (namely, before elongation), specifically, 15 mm. $L_{20}$ represents the grip distance in a state where a tensile load of 20 N is applied (namely during elongation).]

In the tensile test for measuring a 20 N axial direction stretch rate, a part of the knee supporter is fixed to a tensile tester with a grip width of 15 mm and a grip distance of 15 mm, and stretched at a tensile speed of 15 mm/min.

Further, in a case where it is difficult to perform the tensile test on a part of a knee supporter, a test piece of 30 mm square may be cut out from the knee supporter and the test may be performed on the cut out test piece.

The number of tests is five, the average value is calculated from three measurement values excluding the maximum value and the minimum value from the five measurement values, and this average value is adopted as a "20 N axial direction stretch rate".

A general tensile tester may be used as an apparatus for the tensile test, and for example, an Autograph "AGS-X 1kN" manufactured by Shimadzu Corporation may be used.

The femoral side posterior surface part (D) preferably has a 20 N axial direction stretch rate of from 150% to 850%.

When the 20 N axial direction stretch rate of the femoral side posterior surface part (D) is 150% or more, the ease of bending and stretching movements of the knee joint is improved.

When the 20 N axial direction stretch rate of the femoral side posterior surface part (D) is 850% or less, dislocation of the femoral side posterior surface part (D) is suppressed.

The tibial side posterior surface part (F) has preferably a 20 N axial direction stretch rate of from 150% to 850%.

When the 20 N axial direction stretch rate of the tibial side posterior surface part (F) is 150% or more, the ease of bending and stretching movements of the knee joint is improved.

When the 20 N axial direction stretch rate of the tibial side posterior surface part (F) is 850% or less, dislocation of the tibial side posterior surface part (F) is suppressed.

The maximum point elongation in the axial direction of the femoral side posterior surface part (D) is preferably from 210% to 850%, and more preferably from 420% to 750%.

When the maximum point elongation in the axial direction of the femoral side posterior surface part (D) is 210% or more, it becomes easy to follow an extension and contraction of the muscles in bending and stretching movements of the knee joint, and as a consequence the ease of bending and stretching movements of the knee joint is improved.

When the maximum point elongation in the axial direction of the femoral side posterior surface part (D) is 850% or less, dislocation of the femoral side posterior surface part (D) is further suppressed.

Also, the maximum point elongation in the axial direction of the tibial side posterior surface part (F) is preferably from 210% to 850%, and more preferably from 420% to 750%.

When the maximum point elongation in the axial direction of the tibial side posterior surface part (F) is 210% or more, it becomes easy to follow an extension and contraction of the muscles in bending and stretching movements of the knee joint, and as a consequence the ease of bending and stretching movements of the knee joint is improved.

When the maximum point elongation in the axial direction of the tibial side posterior surface part (F) is 850% or less, dislocation of the femoral side posterior surface part (D) is further suppressed.

In this regard, in the tensile test for measuring a maximum point elongation, a part of the knee supporter is fixed to a tensile tester with a grip width of 15 mm and a grip distance of 15 mm, and stretched at a tensile speed of 15 mm/min.

Further, in a case where it is difficult to perform the tensile test on a part of a knee supporter, a test piece of 30 mm square may be cut out from the knee supporter and the test may be performed on the cut out test piece.

The number of tests is five, the average value is calculated from three measurement values excluding the maximum value and the minimum value from the five measurement values, and this average value is adopted as a "maximum point elongation".

A general tensile tester may be used as an apparatus for the tensile test, and for example, an Autograph "AGS-X 1kN" manufactured by Shimadzu Corporation may be used.

A tubular supporter main body is preferably continuously manufactured by circular knitting.

By doing so, an effect of improving fitting sensation at the time of wearing may be obtained without causing an uncomfortable feeling due to protrusions formed by seams, compared to a case where parts constituting a tubular supporter main body are prepared individually and sewn together. Furthermore, when the parts are continuously manufactured by circular knitting, the effect that the overall stretch rate of a tubular supporter main body is easily secured may be also obtained.

Focusing on the structure of a tubular supporter main body, the tubular supporter main body preferably has a seamless structure from the viewpoints of ensuring fitting sensation at the time of wearing and stretch rate as described above. In this regard, a seamless structure means an integrated structure having neither axial seam (for example, a seam for forming a tubular shape by sewing), nor circumferential seam (for example, seams for sewing the parts together).

A tubular supporter main body having a seamless structure may be formed, for example, by continuously producing a tubular supporter main body by circular knitting.

A knee supporter of the embodiment preferably further includes a femoral side rib top part disposed on the femoral side with respect to the tubular supporter main body, and a tibial side rib top part disposed on the tibial side with respect to the tubular supporter main body. By doing so, slipping down or lifting up of the knee supporter may be suppressed more effectively.

When the knee supporter of the embodiment is provided with a femoral side rib top part and a tibial side rib top part, the femoral side rib top part and the tibial side rib top part may be connected with the supporter main body by sewing or may be produced continuously with the supporter main body by circular knitting.

At least at a part of, at least, the back side of the femoral side rib top part (i.e., the surface facing the leg. The same holds hereinafter.), a resin layer (e.g., a silicone rubber layer, an acrylic resin layer, or an acrylic urethane resin layer) is preferably provided from the viewpoint of suppression of slipping down of the knee supporter. The resin layer may be formed by, for example, printing. The resin layer may be provided on the back side of the tibial side rib top part.

A knee supporter may include a member other than the above.

Examples of such other member include a rod-like support member (stay) placed at a position corresponding to the side of the knee to protect the knee by appropriately controlling the movement of the knee; and a fixing belt for fixing the supporter main body to the leg.

Especially, by providing a fixing belt on the surface of the femoral side rib top part (the surface opposite to the surface facing the leg), slipping down of the knee supporter may be inhibited more effectively. It is preferable that the fixing belt is provided with a member for adjusting the tightening force to the leg (for example, a hook-and-loop fastener).

For the knee anterior surface part (A) of the embodiment, the ratio of the 80% axial direction elastic modulus to the 80% circumferential direction elastic modulus (hereinafter also referred to as [80% axial direction elastic modulus/80% circumferential direction elastic modulus]) is preferably 0.4 or higher, more preferably 0.5 or higher, further preferably 0.7 or higher, still further preferably 1 or higher, and still further preferably beyond 1. When the [80% axial direction elastic modulus/80% circumferential direction elastic modulus] is 0.5 or higher, the sense of fixation to the knee joint is improved.

From the viewpoint of improvement of sense of fixation to the knee joint, the ratio [80% axial direction elastic modulus/80% circumferential direction elastic modulus] of the knee anterior surface part (A) is preferably 1.2 or higher, and more preferably 1.5 or higher.

Meanwhile, from the viewpoint of improvement of fitting sensation with respect to the knee joint, the ratio [80% axial direction elastic modulus/80% circumferential direction elastic modulus] of the knee anterior surface part (A) is preferably 5.0 or less, more preferably 4.0 or less, and especially preferably 3.0 or less.

The method of measuring an 80% circumferential direction elastic modulus is herein the same as the method of measuring an 80% axial direction elastic modulus except that the test direction is changed to the circumferential direction.

For the knee posterior surface part (B) of the embodiment, the ratio of the 80% axial direction elastic modulus to the 80% circumferential direction elastic modulus [80% axial direction elastic modulus/80% circumferential direction elastic modulus] preferably exceeds 1. This improves the sense of fixation to the knee joint.

From the viewpoint of improvement of sense of fixation to the knee joint, the ratio [80% axial direction elastic modulus/80% circumferential direction elastic modulus] of the knee posterior surface part (B) is preferably 1.5 or higher, and more preferably 2.0 or higher.

Meanwhile, from the viewpoint of improvement of fitting sensation with respect to the knee joint, the ratio [80% axial direction elastic modulus/80% circumferential direction elastic modulus] of the knee posterior surface part (B) is preferably 6.0 or less, and more preferably 5.0 or less.

For the femoral side posterior surface part (D) of the embodiment, the ratio of the 80% axial direction elastic modulus to the 80% circumferential direction elastic modulus [80% axial direction elastic modulus/80% circumferential direction elastic modulus] is preferably less than 1. This improves the ease of bending and stretching movements of the knee joint.

From the viewpoint of improvement of ease of bending and stretching movements of the knee joint, the ratio [80% axial direction elastic modulus/80% circumferential direction elastic modulus] of the femoral side posterior surface part (D) is preferably 0.8 or less, more preferably 0.5 or less, and especially preferably 0.4 or less.

Meanwhile, from the viewpoint of manufacturing suitability, the ratio [80% axial direction elastic modulus/80% circumferential direction elastic modulus] of the femoral side posterior surface part (D) is preferably 0.1 or more.

For the tibial side posterior surface part (F) of the embodiment, the ratio of the 80% axial direction elastic modulus to the 80% circumferential direction elastic modulus [80% axial direction elastic modulus/80% circumferential direction elastic modulus] is preferably less than 1. This improves the ease of bending and stretching movements of the knee joint.

From the viewpoint of improvement of ease of bending and stretching movements of the knee joint, the ratio [80% axial direction elastic modulus/80% circumferential direction elastic modulus] of the tibial side posterior surface part (F) is preferably 0.8 or less, more preferably 0.5 or less, and especially preferably 0.4 or less.

Meanwhile, from the viewpoint of manufacturing suitability, the ratio [80% axial direction elastic modulus/80% circumferential direction elastic modulus] of the femoral side back side support part is preferably 0.1 or more.

Next, specific examples of the embodiment will be described referring to the drawings, provided that the embodiment be not limited to the following specific examples.

Figure 2:
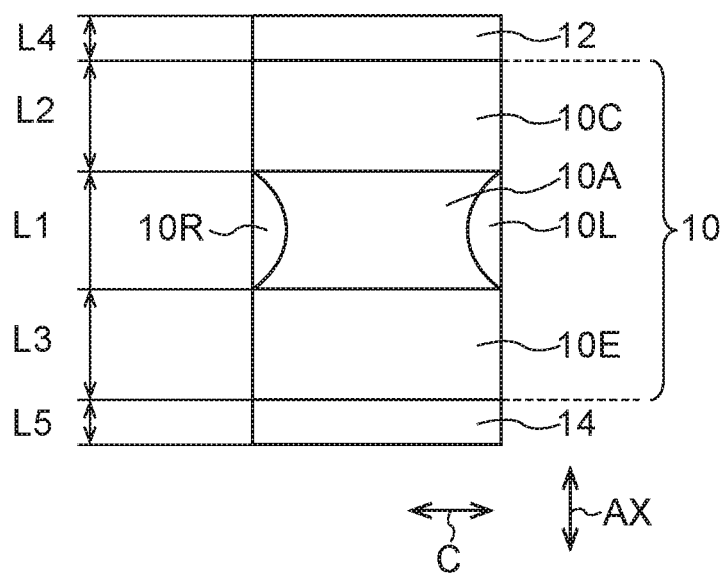
FIG. 2 is a schematic front view of a knee supporter according to a specific example of the invention.

FIG. 1 is a schematic perspective view of a knee supporter with respect to the specific example; FIG. 2 is a schematic front view of a knee supporter with respect to the specific example; and FIG. 3 is a schematic rear view of a knee supporter with respect to the specific example.

Figure 3:
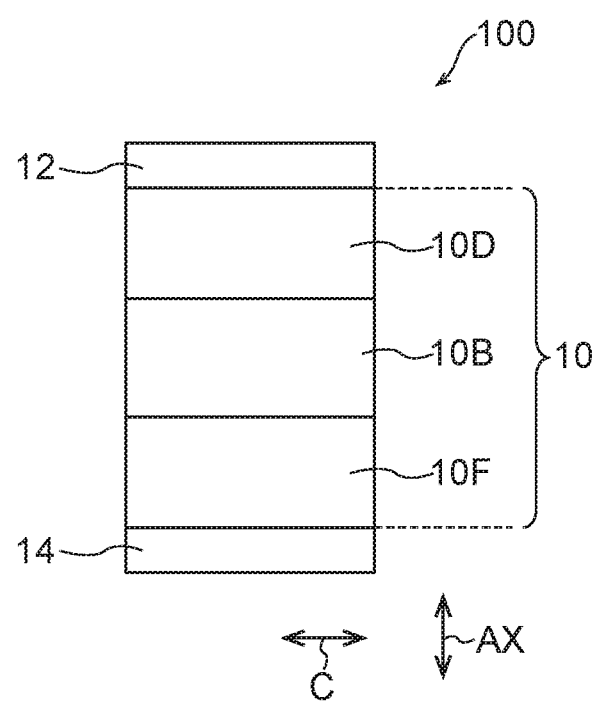
FIG. 3 is a schematic rear view of a knee supporter according to a specific example of the invention.

In FIGS. 1 to 3, the axial direction of the tubular supporter main body is indicated by the arrow AX, and the circumferential direction of the tubular supporter is indicated by the arrow C.

Further, in FIG. 1, the forward direction is indicated by the arrow FR and the upward direction is indicated by the arrow UP.

The "forward direction" refers herein to the direction from the back side of the knee (i.e., from the popliteal side) to the patella side, and "upward direction" refers to the direction from the tibial side to the femoral side.

As shown in FIGS. 1 to 3, the knee supporter 100 with respect to this specific example is provided with a tubular supporter main body 10.

The tubular supporter main body 10 is configured by:
a knee anterior surface part 10A that supports the anterior surface of the knee,
a knee posterior surface part 10B that supports the posterior surface of the knee,
a pair of knee lateral parts 10R and 10L which adjoin the knee anterior surface part 10A and the knee posterior surface part 10B, and support the lateral surface of the knee,
a femoral side anterior surface part 10C that supports an anterior surface of the femoral side, with respect to the knee, of the leg,
a femoral side posterior surface part 10D that supports a posterior surface of the femoral side,
a tibial side anterior surface part 10E that supports an anterior surface of the tibial side, with respect to the knee, of the leg, and
a tibial side posterior surface part 10F that supports a posterior surface of the femoral side.

In this regard, a knee anterior surface part 10A, a knee posterior surface part 10B, a femoral side anterior surface part 10C, a femoral side posterior surface part 10D, a tibial side anterior surface part 10E, and a tibial side posterior surface part 10F are respectively specific examples of the knee anterior surface part (A), the knee posterior surface part (B), the femoral side anterior surface part (C), the femoral side posterior surface part (D), the tibial side anterior surface part (E), and the tibial side posterior surface part (F).

The knee supporter 100 further includes a femoral side rib top part 12 disposed on the femoral side of the tubular supporter main body 10, and a tibial side rib top part 14 disposed on the tibial side of the tubular supporter main body 10.

In the specific examples, the respective parts are integrated to constitute a tubular knee supporter 100.

Furthermore, in the specific example, the 80% axial direction elastic modulus of each of a knee anterior surface part 10A, a knee posterior surface part 10B, a femoral side anterior surface part 10C, a femoral side posterior surface part 10D, a tibial side anterior surface part 10E, and a tibial side posterior surface part 10F satisfies Formula (1) to Formula (3), Formula (4X), and Formula (5X) (first mode); or satisfies Formula (1) to Formula (3), Formula (4Y), and Formula (5Y) (second mode); or satisfies Formula (1) to Formula (3), Formula (4X), and Formula (5Y) (third mode).

A more preferable embodiment in terms of the 80% axial direction elastic modulus of each part is as described above.

In a knee supporter 100, the boundary line between each part is not necessarily required to be clear outwardly. Even when the boundary line between each part is not clear outwardly, the boundary line between each part may be distinguished by the difference in elastic modulus of each part.

The femoral side rib top part 12, the supporter main body 10, and the tibial side rib top part 14 in the knee supporter 100, are continuously formed by circular knitting to have a seamless structure. As a result, the fitting sensation at the time of wearing is particularly excellent.

However, the embodiment is not limited to this example, and it is also possible to manufacture a supporter main body by sewing together the respective parts prepared in advance as individual and independent components.

Also, the whole or part of the knee supporter 100 including the femoral side rib top part 12, the supporter main body 10, and the tibial side rib top part 14 may be continuously produced by circular knitting. In other words, the structure of the whole or part of the knee supporter 100 may be a seamless structure.

The shape of each of the pair of knee lateral support parts 10R and 10L in this specific example is a shape surrounded by a boundary line with the knee anterior surface part 10A forming an arc, and a boundary line with the knee posterior surface part 10B forming a straight line (chord) from the viewpoint of ease of bending and stretching of the knee. However, the shapes of the pair of knee lateral support parts 10R and 10L are not limited to this shape.

Further, the pair of knee lateral support parts 10R and 10L may be omitted.

Examples of the material of the knee supporter 100 include chemical fibers of polyester, polypropylene, polyurethane, polyolefin, polyolefin elastomer, polyamide, rayon, polyacrylonitrile, cupra, acetate, promix, aramid, silicone, and the like; natural fibers, such as cotton, wool, silk, hemp, and rayon; natural rubber; and polyvinyl chloride.

Among them, polyester, polyurethane, polyamide, polyolefin, polyolefin elastomer, silicone, or natural rubber is preferable, and from the viewpoint of long-term durability, polyester, polyurethane, polyamide, polyolefin, or polyolefin elastomer is more preferable.

Examples of a yarn for the knee supporter 100 include monofilament; multifilament; SCY (Single Covering Yarn) coated with polyurethane or rubber; and DCY (Double Covering Yarn) coated with polyurethane or rubber.

Each of the knit structure of the knee anterior surface part 10A, the knit structure of the knee posterior surface part 10B, the pair of knee lateral support parts 10R and 10L, the knit structure of the femoral side anterior surface part 10C, the knit structure of the femoral side posterior surface part 10D, the knit structure of the tibial side anterior surface part 10E, and the knit structure of the tibial side posterior surface part 10F is preferably a knit structure including a float stitch structure as described above.

As a knit structure of the femoral side rib top part 12 or the tibial side rib top part 14, a rib stitch structure or a non-run knit structure is preferable.

The surface of the knit structure of the knee supporter 100 may be impregnated with a resin, or may be printed.

The knee supporter 100 may include a structure other than the knit structure.

Examples of such other structure may include a structure including a neoprene rubber, and a structure including a neoprene rubber laminated body.

With respect to the material, yarn, and knit structure for the knee supporter 100, publicly known materials, yarns, and knit structures described in, for example, JP-A No. 2011-130784, JP-A No. 2007-9362, JP-A No. 2010-13765, JP-A No. 2000-116697, and JP-A No. 2007-54126 may be referred to.

Next, a preferable size of the knee supporter 100 will be described referring to FIG. 2.

In this regard, an axial direction length herein means an axial direction length when not stretched, and an average circumferential length herein means an average circumferential length when not stretched.

The axial direction length L1 of a tubular portion composed of the knee anterior surface part 10A, the knee posterior surface part 10B, and a pair of the knee lateral support parts 10R and 10L (hereinafter also referred to as "knee support part"; when the pair of the knee lateral support parts 10R and 10L are omitted, a tubular portion composed of the knee anterior surface part 10A and the knee posterior surface part 10B) is preferably from 60 mm to 200 mm, and more preferably from 80 mm to 180 mm.

The axial direction length L2 of a tubular portion composed of the femoral side anterior surface part 10C and the femoral side posterior surface part 10D (hereinafter also referred to as "femoral side support part") is preferably from 30 mm to 200 mm, and more preferably from 30 mm to 150 mm.

The axial direction length L3 of a tubular portion composed of the tibial side anterior surface part 10E and the tibial side posterior surface part 10F (hereinafter also referred to as "tibial side support part") is preferably from 30 mm to 200 mm, and more preferably from 30 mm to 150 mm.

The axial direction length L4 of the femoral side rib top part 12 is preferably from 10 mm to 100 mm, more preferably from 10 mm to 80 mm, and especially preferably from 20 mm to 70 mm.

The axial direction length L5 of the tibial side rib top part 14 is preferably from 10 mm to 100 mm, more preferably from 10 mm to 80 mm, and especially preferably from 20 mm to 70 mm.

The (overall) axial direction length of the knee supporter 100 is preferably from 140 mm to 760 mm, and more preferably from 180 mm to 620 mm.

An axial direction length is herein a value expressed by the following Formula.

$$\text{Axial direction length} = (\text{maximum length in the axial direction} + \text{minimum length in the axial direction})/2$$

The average circumferential length of the knee support part is preferably from 100 mm to 300 mm, and more preferably from 150 mm to 280 mm.

The average circumferential length of the femoral side support part is preferably from 100 mm to 400 mm, and more preferably from 150 mm to 350 mm.

The average circumferential length of the tibial side support part is preferably from 100 mm to 350 mm, and more preferably from 100 mm to 300 mm.

The average circumferential length of the femoral side rib top part is preferably from 180 mm to 350 mm, more preferably from 180 mm to 320 mm, and especially preferably from 200 mm to 320 mm.

The average circumferential length of the tibial side rib top part is preferably from 100 mm to 350 mm, and more preferably from 120 mm to 300 mm.

In this regard, an average circumferential length is a value represented by the following Formula.

$$\text{Average circumferential length} = (\text{maximum circumferential length} + \text{minimum circumferential length})/2$$

[Garment]

<Mode A>

A garment according to Mode A which is a mode of the embodiment is a garment including the aforedescribed knee supporter of the embodiment.

With the garment according to the mode A, the same effect as that of the knee supporter of the embodiment may be obtained.

Examples of the garment according to the mode A include bottoms (e.g. for sports, or inner wear), such as spats, tights (for example, sport tights, compression tights, and medical tights), girdles, pantyhose, leggings, trenca, and leg warmers; and bandages.

In the garment according to the mode A, the knee supporter and the portion other than the knee supporter may be sewed or bonded with an adhesive together.

Further, in the garment according to the mode A, the knee supporter and the portion other than the knee supporter may be integrally and continuously manufactured by circular knitting.

<Mode B>

A garment according to Mode B which is another mode of the embodiment is a garment, comprising a tubular joint supporter unit, the tubular joint supporter unit comprising:

a central region in an axial direction of the tubular joint supporter unit, which supports a joint part of a wearer's body;

a one-end side region located at one end side in the axial direction with respect to the central region; and an other-end side region located at another end side in the axial direction with respect to the central region, wherein, in a case in which an elastic modulus in the axial direction when a region is stretched by 80% in the axial direction is defined as an 80% axial direction elastic modulus, a minimum value of the 80% axial direction elastic modulus in the central region is defined as an elastic modulus EC, a minimum value of the 80% axial direction elastic modulus in the one-end side region is defined as an elastic modulus EE1, and a minimum value of the 80% axial direction elastic modulus in the other-end side region is defined as an elastic modulus EE2, the elastic modulus EC is 5 to 50 times as high as at least one of the elastic modulus EE1 or the elastic modulus EE2.

A tubular joint supporter unit in the mode B is superior in sense of fixation to the joint and suppresses dislocation at the time of wearing owing to the above configuration.

More particularly, when the elastic modulus EC is at least five times as high as at least one of the elastic modulus EE1 or the elastic modulus EE2, the sense of fixation to the joint part is improved.

Further, when the elastic modulus EC is at most 50 times as high as at least one of the elastic modulus EE1 or the elastic modulus EE2, it is possible to suppress dislocation at the time of wearing (more specifically, dislocation of the one-end side region and the other-end side region).

Further, when the elastic modulus EC is at most 50 times as high as at least one of the elastic modulus EE1 or the elastic modulus EE2, the effect of improving the ease of bending and stretching movements of a joint is obtained.

Further, when the elastic modulus EC is at most 50 times as high as at least one of the elastic modulus EE1 or the elastic modulus EE2, excessive tightening (compression) against a joint is suppressed further, and the effect that the comfort at the time of wearing is improved may be also obtained.

From the viewpoint of obtaining the above-described effect more effectively, the elastic modulus EC is preferably 5 times to 40 times as high as at least one of the elastic modulus EE1 or the elastic modulus EE2.

In a case in which, in the tubular joint supporter unit according to the mode B, a semicircular side including an outer side when a joint is bent is defined as an anterior surface part, and a semicircular side including an inner side when a joint is bent is defined as a posterior surface part, it is preferable that:

a region exhibiting the elastic modulus EE1 is positioned in the posterior surface part in the one-end side region, and a region exhibiting the elastic modulus EE2 is positioned in the posterior surface part in the other-end side region.

According to this mode, the comfort at the time of wearing and the ease of bending and stretching movements of a joint are further improved.

The elastic modulus EE1 and the elastic modulus EE2 are each preferably 0.001 MPa or more from the viewpoint of better suppression of dislocation at the time of wearing, and more preferably 0.01 MPa or more.

The elastic modulus EE1 and the elastic modulus EE2 are each preferably 0.1 MPa or less, and more preferably 0.08 MPa or less.

In addition, a preferred mode of a knee supporter of the embodiment may be applied to a tubular joint supporter unit according to the mode B.

A garment according to the mode B may be a garment configured by only a joint supporter unit (i.e., a supporter), or a garment provided with a joint supporter unit as a part of the garment.

In this regard, examples of the garment provided with a joint supporter unit as a part of the garment include bottoms (e.g., bottoms for sports, or inner wear), such as spats, tights (e.g., sport tights, compression tights, and medical tights), girdles, pantyhose, leggings, trenca, and leg warmers; tops, such as an underwear, a shirt, and a compression shirt; socks; gloves; a finger stall; and bandages.

In the garment according to the mode B, the joint supporter unit and the portion other than the joint supporter unit may be sewed or bonded with an adhesive together.

Further, in the garment according to the mode B, the joint supporter unit and the portion other than the joint supporter unit may be integrally and continuously manufactured by circular knitting.

Examples of a joint at a joint part include the knee joint, the elbow joint, the wrist joint, the finger joint, the toe joint, the talocrural joint, the talar joint, the neck joint, the shoulder joint, and the hip joint.

As a joint on which the central region of the joint supporter unit is worn, the knee joint, the elbow joint, the wrist joint, the finger joint, or the toe joint is preferable from the viewpoint of pain relief, and the knee joint is more preferable. The knee joint, the elbow joint, the wrist joint, the finger joint, and the toe joint have a common feature that each is configured by three or more bones.

When a joint part is compressed by applying compression by a compression applying region, the arrangement of the bones of the joint is optimized such that parts positioned around the joint, excluding the joint part, may be controlled to move easily. This gives an effect of pain relief.

The knee joint, the elbow joint, the wrist joint, the finger joint, or the toe joint is a joint having a wider movable range as compared with other joints. With respect to the knee joint, the elbow joint, the wrist joint, the finger joint, and the toe joint, the arrangement of the bones tends to be disordered as the muscles decline, therefore it is particularly useful to wear a supporter on the joint to impart a sense of support.

Especially, with respect to the knee joint, since it supports the weight of the human body in walking, a heavy load is likely to be applied, and the arrangement of the bones is liable to be disordered. Therefore, the effect according to the mode B is particularly effectively exhibited when the central region of the joint supporter unit is worn on the knee joint.

According to the mode B, as a means for adjusting the elastic modulus EC so that it is 5 to 50 times as high as at least one of the elastic modulus EE1 or the elastic modulus EE 2, there are, for example, a means for forming a part of a tubular joint supporter unit with a concave-convex structure region, a woven fabric structure, or a resin sheet (e.g., a film), and a means for forming a part of a tubular joint supporter unit with a knitted fabric using a yarn with a high stretch rate.

It is preferable that each of the region exhibiting the elastic modulus EE1 and the region exhibiting the elastic modulus EE2 includes a concave-convex structure region (preferably a concave-convex knitted fabric structure described below). By doing so, the relationship that the elastic modulus EC is 5 to 50 times as high as at least one of the elastic modulus EE1 or the elastic modulus EE2 may be more easily achieved.

When each of the region exhibiting the elastic modulus EE1 and the region exhibiting the elastic modulus EE2 includes a concave-convex structure region (preferably a concave-convex knitted fabric structure described below), it becomes easier for each of the region exhibiting the elastic modulus EE1 and the region exhibiting the elastic modulus EE2 to achieve that the maximum point elongation in the axial direction is from 210% to 850% (preferably from 420% to 750%).

When the maximum point elongation in the axial direction of each of the region exhibiting the elastic modulus EE1 and the region exhibiting the elastic modulus EE2 is 210% or more, it becomes easy to follow the extension and contraction of the muscles in bending and stretching movements of the joint, and as a consequence the bending and stretching movements of the joint become easier.

When the maximum point elongation in the axial direction of each of the region exhibiting the elastic modulus EE1 and the region exhibiting the elastic modulus EE2 is 50% or less, dislocation at the time of wearing is further suppressed.

In this regard, a concave-convex structure region is a region including a concave-convex structure, which is a structure having a concave-convex shape.

Examples of a concave-convex structure included in a concave-convex structure region include a knitted fabric structure (hereinafter also referred to as "knitted fabric"), a woven fabric structure (hereinafter also referred to as "woven fabric"), and a resin sheet (e.g., a film). Among them, a knitted fabric and a woven fabric are preferably used as a concave-convex structure, and a knitted fabric is used more preferably. Further, a single concave-convex structure may be used in a concave-convex structure region, or a combination of a plurality of concave-convex structures may be used.

Among them, as a concave-convex structure region including a concave-convex structure, a concave-convex knitted fabric region including a concave-convex knitted fabric, a concave-convex woven fabric region including a concave-convex woven fabric, or a concave-convex structure region including a concave-convex knitted fabric and a concave-convex woven fabric is preferable from the viewpoints of reduction of uncomfortable feeling at the time of wearing, improvement of permeability, and improvement of motion followability, and a concave-convex knitted fabric region including a concave-convex knitted fabric is more preferable.

The concave-convex knitted fabric region is a region including a concave-convex knitted fabric which is a knit structure having a concave-convex shape.

A concave-convex knitted fabric included in a concave-convex knitted fabric region may be a single concave-convex knitted fabric, or a combination of two or more kinds of concave-convex knitted fabrics.

The area of a concave-convex knitted fabric region is preferably 4 cm$^2$ or more in terms of the area of the concave-convex knitted fabric region in a stretched state at the time of wearing, and more preferably 6 cm$^2$ or more.

The length in the circumferential direction of a concave-convex knitted fabric region is preferably equal to or longer than 1/6 of the length of the whole circumference of the joint supporter unit (more particularly, the length of the whole circumference crossing the concave-convex knitted fabric region), and more preferably 1/3 or longer.

In this regard, the length in the circumferential direction of a concave-convex knitted fabric region means, in a case in which the concave-convex knitted fabric region is placed divided into segments in the circumferential direction, total length of the segments collected without overlapping in the circumferential direction.

A plurality of concave-convex knitted fabric regions may be placed in the one-end side region and/or the other-end side region. When a plurality of concave-convex knitted fabric regions are placed in the one-end side region and/or the other-end side region, the arrangement thereof is not particularly limited.

There is no particular restriction on the shape of the concave-convex knitted fabric region and the shape of the boundary line with an adjacent region. They may be determined from the viewpoint of design, if appropriate.

In the mode B, the joint supporter unit includes a central region and a concave-convex structure region (e.g., a concave-convex knitted fabric region). The joint supporter unit may include a region other than the central region and the concave-convex structure region (other region).

When it includes another region in addition to the central region and the concave-convex structure region, such other region may be configured by a woven fabric, a resin sheet, a knit structure different from the central region and the concave-convex structure region, or the like. Among others, a knit structure or a woven fabric is preferable from the viewpoint of reduction of skin stress, and a knit structure using an elastic yarn is more preferable. However, the structure of such other region is selected such that the elastic modulus EC is 5 to 50 times as high as at least one of the elastic modulus EE1 or the elastic modulus EE2, if appropriate.

It is preferable that a concave-convex knitted fabric region includes a repeated tuck stitch structure.

In this regard, a repeated tuck stitch means a knitting method by which tuck stitching is repeated.

When a concave-convex knitted fabric region includes a repeated tuck stitch structure, the stretchability may be adjusted easier.

It is also preferable that the concave-convex knitted fabric in a concave-convex knitted fabric region includes a float stitch structure.

A float stitch structure in a concave-convex knitted fabric is capable of extending and contracting better than a knit structure other than a float stitch structure. The reason why a concave-convex knitted fabric including a float stitch structure is soft is conceivably that, even when the concave-convex knitted fabric region is extended in wearing, there remains a leeway for further extension (i.e., concavity and convexity) in the float stitch structure in the concave-convex knitted fabric. When the leeway for extension touches the skin, it gives a soft touch. Also, from the viewpoint of ease of manufacturing a concave-convex knitted fabric, it is preferable to form a concave-convex knitted fabric by adding a float stitch structure.

It is also preferable that a concave-convex knitted fabric in a concave-convex knitted fabric region is knitted with an elastic yarn, and more preferable that the concave-convex knitted fabric is a concave-convex knitted fabric including a float stitch structure using an elastic yarn. By using an elastic yarn, a concave-convex knitted fabric may be made softer.

Examples of the elastic yarn include those of polyurethane, a polyolefin elastomer, natural rubber, and silicone. Among them, from the viewpoint of better elasticity, those of polyurethane, a polyolefin elastomer, and natural rubber are preferable.

From the viewpoint of high suitability in manufacturing an integrated joint supporter unit by circular knitting, it is preferable to add a float stitch structure in the axial direction.

Also, it is preferable that a concave-convex knitted fabric region has an elongated concave portion. The elongated shape referred to herein is naturally the shape of a concave portion in a plan view.

Among the concave-convex knitted fabric regions, especially the bottom portion of the concave portion tends to stretch easily. For this reason, a concave-convex knitted fabric region having an elongated concave portion tends to stretch easily in the width direction of the concave portion. Therefore, when a concave-convex knitted fabric region has an elongated concave portion, the entire area of the concave-convex knitted fabric region tends to stretch easily, so that the motion followability is further improved.

A concave-convex knitted fabric region preferably has a plurality of elongated concave portions.

It is preferable that a concave-convex knitted fabric region has a plurality of elongated concave portions, and the length direction of each of the plurality of elongated concave portions is substantially parallel to the circumferential direction of a tubular joint supporter unit.

In this case, the width direction of the elongated concave portion corresponds to the axial direction of the joint supporter unit. For this reason, the concave-convex knitted fabric region stretches easily in the axial direction of the joint supporter unit, so that the motion followability is improved.

Further it is also advantageous in terms of manufacturing suitability for manufacturing a joint supporter unit by circular knitting that a concave-convex knitted fabric region has a plurality of elongated concave portions with the aforedescribed longitudinal direction. More particularly, when a joint supporter unit is manufactured by circular knitting, the aforedescribed elongated concave portion (namely, an elongated concave portion, whose longitudinal direction is substantially parallel to the circumferential direction of the joint supporter unit) may be manufactured easily by knitting while skipping one or more stitches in the circumferential direction using float stitch.

EXAMPLES

The invention will be specifically described below by way of Examples, provided that the invention be not limited to the Examples.

Example 1

A supporter X having the same configuration as the above knee supporter 100 was prepared.

The supporter X was produced by continuously knitting a femoral side rib top part, a tubular supporter main body, and a tibial side rib top part by circular knitting.

The tubular supporter main body was produced to have a knit structure including a float stitch structure. In doing so, the density and distribution of float yarns were varied among the respective parts constituting the tubular supporter main body (a knee anterior surface part (A), a knee posterior surface part (B), a pair of knee lateral support parts, a femoral side anterior surface part (C), a femoral side posterior surface part (D), a tibial side anterior surface part (E), and a tibial side posterior surface part (F)) so that the axial direction elastic modulus of each part satisfy Formulae (1) to (3), Formula (4X), and Formula (5X).

In addition, each of the knit structures of a femoral side rib top part and a tibial side rib top part was formed as a non-run knit structure.

The materials of the supporter X were nylon and polyurethane.

The sizes of the supporter X in a not-stretched state are as follows.

Knee support part: axial direction length 130 mm, average circumferential length 220 mm Femoral side support part: axial direction length 50 mm, average circumferential length 208 mm Tibial side support part: axial direction length 45 mm, average circumferential length 195 mm Femoral side rib top part: axial direction length 30 mm, average circumferential length 280 mm Tibial side rib top part: axial direction length 20 mm, average circumferential length 240 mm For each part of the supporter X, the 80% axial direction elastic modulus, the 80% circumferential direction elastic modulus, the 20 N axial direction stretch rate, and the 20 N circumferential direction stretch rate were measured.

The measurement methods for an 80% axial direction elastic modulus, an 80% circumferential direction elastic modulus, and a 20 N axial direction stretch rate are as described above.

The measurement method of a 20N circumferential direction stretch rate is the same as the measuring method of a 20N axial direction stretch rate except that the measurement direction is the circumferential direction.

The results are shown in Table 1 below.

TABLE 1

|  | Axial direction | | Circumferential direction | |
| --- | --- | --- | --- | --- |
| Supporter X | 80% Elastic modulus (MPa) | 20 N Stretch rate (%) | 80% Elastic modulus (MPa) | 20 N Stretch rate (%) |
| Knee anterior surface part (A) | 0.58 | 184 | 0.29 | 188 |
| Knee posterior surface part (B) | 0.68 | 111 | 0.19 | 201 |
| Femoral side anterior surface part (C) | 0.21 | 135 | 0.19 | 212 |
| Femoral side posterior surface part (D) | 0.02 | 488 | 0.09 | 236 |
| Tibial side anterior surface part (E) | 0.21 | 135 | 0.19 | 212 |
| Tibial side posterior surface part (F) | 0.02 | 488 | 0.09 | 236 |
| (B)/(A) | 1.2 | — | — | — |
| (A)/(C) | 2.8 | — | — | — |
| (C)/(D) | 10.5 | — | — | — |
| (A)/(E) | 2.8 | — | — | — |
| (E)/(F) | 10.5 | — | — | — |
| (E)/(D) | 10.5 | — | — | — |
| (C)/(F) | 10.5 | — | — | — |
| (B)/(D) | 34.0 | — | — | — |
| (B)/(F) | 34.0 | — | — | — |

—Explanation of Table 1 and Tables 3 and 4 Below—

The 80% elastic modulus in the column of axial direction represents an 80% axial direction elastic modulus, and the 80% elastic modulus in the column of circumferential direction represents an 80% circumferential direction elastic modulus.

The 20 N stretch rate in the column of axial direction represents a 20 N axial direction stretch rate, and the 20 N stretch rate in the column of circumferential direction represents a 20 N circumferential direction stretch rate.

As shown in Table 1, the supporter X which was a specific example of the knee supporter according to the invention satisfied Formulae (1) to (3). Therefore, the supporter X is expected to be superior in sense of fixation to the knee joint and ease of bending and stretching movements of the knee joint.

Further, it is obvious that the supporter X satisfied Formula (4X), Formula (5X), Formulae (6) to (9), Formulae (1a) to (3a), Formula (4Xa), and Formula (5Xa). Therefore, the supporter X is expected to be especially superior in sense of fixation to the knee joint, and ease of bending and stretching movements of the knee joint, and further in comfort (more particularly, fitting sensation improvement, dislocation suppression, and compression suppression).

Next, the supporter X was actually worn for two days by a total of five test subjects consisting of four male adults and one female adult, and a hearing was held for each test subject with respect to the sensation of wearing.

As a result, from each test subject, a sensory opinion to the effect that the supporter X was superior, especially in terms of the sense of fixation to the knee joint and ease of bending and stretching movements of the knee joint, and furthermore, superior in comfort (more specifically, fitting sensation improvement, dislocation suppression, and compression suppression), was obtained.

Examples 2 to 6

Each supporter having the size in a not stretched state specified in the following Table 2 and having the same configuration as the aforementioned knee supporter 100 was prepared.

Each supporter was produced by continuously knitting a femoral side rib top part, a tubular supporter main body, and a tibial side rib top part by circular knitting.

The tubular supporter main body was produced to have a knit structure including a float stitch structure.

In doing so, in Examples 2 to 4, the density and distribution of float yarns were varied among the respective parts constituting the tubular supporter main body (a knee anterior surface part (A), a knee posterior surface part (B), a pair of knee lateral support parts, a femoral side anterior surface part (C), a femoral side posterior surface part (D), a tibial side anterior surface part (E), and a tibial side posterior surface part (F)) so that the axial direction elastic modulus of each part satisfied Formulae (1) to (3), Formula (4X), and Formula (5X); and in Examples 5 and 6, so that the axial direction elastic modulus of each part satisfied Formulae (1) to (3), Formula (4Y), and Formula (5Y).

In addition, each of the knit structures of a femoral side rib top part and a tibial side rib top part was formed as a non-run knit structure.

The materials of each supporter are nylon and polyurethane.

TABLE 2

| | | Example 2 | Example 3 | Example 4 | Example 5 | Example 6 |
|---|---|---|---|---|---|---|
| Axial direction length (mm) | Knee support part (L1) | 113 | 117 | 121 | 119 | 127 |
| | Femoral side support part (L2) | 56 | 38 | 34 | 35 | 34 |
| | Tibial side support part (L3) | 40 | 37 | 37 | 37 | 38 |
| | Femoral side rib top part (L4) | 51 | 51 | 45 | 48 | 48 |
| | Tibial side rib top part (L5) | 26 | 24 | 23 | 24 | 25 |
| Average circumferential length (mm) | Knee support part | 190 | 185 | 175 | 174 | 175 |
| | Femoral side support part | 185 | 178 | 175 | 172 | 178 |
| | Tibial side support part | 178 | 181 | 160 | 161 | 164 |
| | Femoral side rib top part | 187 | 186 | 189 | 190 | 199 |
| | Tibial side rib top part | 170 | 171 | 171 | 163 | 173 |

For each part of each supporter, measurements of an 80% axial direction elastic modulus, an 80% circumferential direction elastic modulus, a 20 N axial direction stretch rate, and a 20 N circumferential direction stretch rate were carried out in the same manner as in Example 1.

The results are shown in the following Tables 3 and 4.

TABLE 3

| | Example 2 | | | | Example 3 | | | | Example 4 | | | |
|---|---|---|---|---|---|---|---|---|---|---|---|---|
| | Axial direction | | Circumferential direction | | Axial direction | | Circumferential direction | | Axial direction | | Circumferential direction | |
| | 80% Elastic modulus (MPa) | 20N Stretch rate (%) | 80% Elastic modulus (MPa) | 20N Stretch rate (%) | 80% Elastic modulus (MPa) | 20N Stretch rate (%) | 80% Elastic modulus (MPa) | 20N Stretch rate (%) | 80% Elastic modulus (MPa) | 20N Stretch rate (%) | 80% Elastic modulus (MPa) | 20N Stretch rate (%) |
| Knee anterior surface part (A) | 0.17 | 261 | 0.22 | 296 | 0.10 | 442 | 0.17 | 327 | 0.60 | 184 | 0.33 | 188 |
| Knee posterior surface part (B) | 0.26 | 158 | 0.19 | 233 | 0.26 | 162 | 0.17 | 263 | 0.47 | 111 | 0.22 | 201 |
| Femoral side anterior surface part (C) | 0.10 | 362 | 0.13 | 408 | 0.09 | 199 | 0.11 | 306 | 0.43 | 135 | 0.20 | 212 |
| Femoral side posterior surface part (D) | 0.03 | 418 | 0.04 | 496 | 0.03 | 531 | 0.05 | 486 | 0.03 | 488 | 0.10 | 236 |
| Tibial side anterior surface part (E) | 0.09 | 162 | 0.10 | 321 | 0.09 | 199 | 0.11 | 306 | 0.43 | 135 | 0.20 | 212 |
| Tibial side posterior surface part (F) | 0.03 | 418 | 0.04 | 496 | 0.03 | 531 | 0.05 | 486 | 0.03 | 488 | 0.10 | 236 |
| (B)/(A) | 1.5 | — | — | — | 2.6 | — | — | — | 0.8 | — | — | — |
| (A)/(C) | 1.7 | — | — | — | 1.1 | — | — | — | 1.4 | — | — | — |
| (C)/(D) | 3.3 | — | — | — | 3.0 | — | — | — | 14.3 | — | — | — |
| (A)/(E) | 1.9 | — | — | — | 1.1 | — | — | — | 1.4 | — | — | — |

TABLE 3-continued

|  | Example 2 | | | | Example 3 | | | | Example 4 | | | |
| --- | --- | --- | --- | --- | --- | --- | --- | --- | --- | --- | --- | --- |
|  | Axial direction | | Circumferential direction | | Axial direction | | Circumferential direction | | Axial direction | | Circumferential direction | |
|  | 80% Elastic modulus (MPa) | 20N Stretch rate (%) | 80% Elastic modulus (MPa) | 20N Stretch rate (%) | 80% Elastic modulus (MPa) | 20N Stretch rate (%) | 80% Elastic modulus (MPa) | 20N Stretch rate (%) | 80% Elastic modulus (MPa) | 20N Stretch rate (%) | 80% Elastic modulus (MPa) | 20N Stretch rate (%) |
| (E)/(F) | 3.0 | — | — | — | 3.0 | — | — | — | 14.3 | — | — | — |
| (E)/(D) | 3.0 | — | — | — | 3.0 | — | — | — | 14.3 | — | — | — |
| (C)/(F) | 3.3 | — | — | — | 3.0 | — | — | — | 14.3 | — | — | — |
| (B)/(D) | 8.7 | — | — | — | 8.7 | — | — | — | 15.7 | — | — | — |
| (B)/(F) | 8.7 | — | — | — | 8.7 | — | — | — | 15.7 | — | — | — |

TABLE 4

|  | Example 5 | | | | Example 6 | | | |
| --- | --- | --- | --- | --- | --- | --- | --- | --- |
|  | Axial direction | | Circumferential direction | | Axial direction | | Circumferential direction | |
|  | 80% Elastic modulus (MPa) | 20N Stretch rate (%) | 80% Elastic modulus (MPa) | 20N Stretch rate (%) | 80% Elastic modulus (MPa) | 20N Stretch rate (%) | 80% Elastic modulus (MPa) | 20N Stretch rate (%) |
| Knee anterior surface part (A) | 0.41 | 165 | 0.24 | 210 | 0.34 | 160 | 0.33 | 188 |
| Knee posterior surface part (B) | 0.54 | 116 | 0.17 | 217 | 0.42 | 124 | 0.16 | 229 |
| Femoral side anterior surface part (C) | 1.08 | 103 | 0.16 | 194 | 1.20 | 100 | 0.22 | 202 |
| Femoral side posterior surface part (D) | 0.07 | 270 | 0.12 | 182 | 0.04 | 311 | 0.09 | 224 |
| Tibial side anterior surface part (E) | 1.08 | 103 | 0.16 | 194 | 1.20 | 100 | 0.22 | 202 |
| Tibial side posterior surface part (F) | 0.07 | 270 | 0.12 | 182 | 0.04 | 311 | 0.09 | 224 |
| (B)/(A) | 1.3 | — | — | — | 1.2 | — | — | — |
| (A)/(C) | 0.4 | — | — | — | 0.3 | — | — | — |
| (C)/(D) | 15.4 | — | — | — | 30.0 | — | — | — |
| (A)/(E) | 0.4 | — | — | — | 0.3 | — | — | — |
| (E)/(F) | 15.4 | — | — | — | 30.0 | — | — | — |
| (E)/(D) | 15.4 | — | — | — | 30.0 | — | — | — |
| (C)/(F) | 15.4 | — | — | — | 30.0 | — | — | — |
| (B)/(D) | 7.7 | — | — | — | 10.5 | — | — | — |
| (B)/(F) | 7.7 | — | — | — | 10.5 | — | — | — |

As shown in Tables 3 and 4, the supporters of Examples 2 to 6 satisfied Formulae (1) to (3). Therefore, these supporters are expected to be superior in sense of fixation to the knee joint and ease of bending and stretching movements of the knee joint.

Also, as obvious from Table 3, the supporters of Examples 2 to 4 satisfy Formula (4X), Formula (5X), Formulae (6) to (9), Formulae (1a) to (3a), Formula (4Xa), and Formula (5Xa). Therefore, the supporters of Examples 2 to 4 are expected to be superior in sense of fixation to the knee joint and ease of bending and stretching movements of the knee joint (especially in sense of fixation to the knee joint), and also superior in comfort.

Also, as obvious from Table 4, the supporters of Examples 5 and 6 satisfy Formula (4Y), Formula (5Y), Formulae (6) to (9), and Formulae (1a) to (3a). Therefore, the supporters of Examples 2 to 4 are expected to be superior in sense of fixation to the knee joint and ease of bending and stretching movements of the knee joint (especially in ease of bending and stretching movements of the knee joint), and also superior in comfort.

Next, for the supporters of Examples 1, and 4 to 6, the maximum point elongations in the axial direction of the femoral side posterior surface part (D) and the tibial side posterior surface part (F) were measured.

As a result, the maximum point elongation in the axial direction of the femoral side posterior surface part (D) of the supporter of Example 1 was 644%, and the maximum point elongation in the axial direction of the tibial side posterior surface part (F) of the supporter of Example 1 was 644%;

the maximum point elongation in the axial direction of the femoral side posterior surface part (D) of the supporter of Example 4 was 724%, and the maximum point elongation in the axial direction of the tibial side posterior surface part (F) of the supporter of Example 4 was 724%;

the maximum point elongation in the axial direction of the femoral side posterior surface part (D) of the supporter of Example 5 was 438%, and the maximum point elongation in the axial direction of the tibial side posterior surface part (F) of the supporter of Example 5 was 438%; and the maximum point elongation in the axial direction of the femoral side posterior surface part (D) of the supporter of Example 6 was 475%, and the maximum point elongation in the axial direction of the tibial side posterior surface part (F) of the supporter of Example 6 was 475%.

Next, each of the supporters of Examples 2 to 5 was actually worn for two days by a total of five test subjects consisting of four male adults and one female adult, and a hearing was held for each test subject with respect to the sensation of wearing for each supporter.

As a result, from each test subject, a sensory opinion to the effect that each supporter was superior, especially in terms of the sense of fixation to the knee joint and ease of bending and stretching movements of the knee joint, and furthermore, superior in comfort was obtained.

The disclosures of Japanese Patent Application No. 2016-020144 and Japanese Patent Application No. 2016-236069 are incorporated herein by reference in their entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A knee supporter, comprising a tubular supporter main body that is configured to be worn on a part of a leg including a knee, the tubular supporter main body comprising:
   a knee anterior surface part (A) that is configured to support an anterior surface of the knee;
   a knee posterior surface part (B) that is configured to support a posterior surface of the knee;
   a femoral side anterior surface part (C) that is configured to support an anterior surface of a femoral side, with respect to the knee, of the leg;
   a femoral side posterior surface part (D) that is configured to support a posterior surface of the femoral side;
   a tibial side anterior surface part (E) that is configured to support an anterior surface of a tibial side, with respect to the knee, of the leg; and
   a tibial side posterior surface part (F) that is configured to support a posterior surface of the tibial side,
   wherein each of the surface parts (A)-(F) in the knee supporter have a density and distribution of yarns with an elastic moduli, when stretched by 80% in the axial direction of the tubular supporter main body, that satisfy the following Formulas (1) to (3):

$1<$ an elastic modulus of the knee posterior surface part$(B)$/an elastic modulus of the knee anterior surface part$(A)$;     Formula (1):

$1<$ an elastic modulus of the femoral side anterior surface part$(C)$/an elastic modulus of the femoral side posterior surface part$(D)$; and     Formula (2):

$1<$ an elastic modulus of the tibial side anterior surface part$(E)$/an elastic modulus of the tibial side posterior surface part$(F)$.     Formula (3):

2. The knee supporter according to claim 1, wherein the elastic moduli in the axial direction of the knee anterior surface part (A), the femoral side anterior surface part (C), and the tibial side anterior surface part (E), when stretched by 80% in the axial direction of the tubular supporter main body, satisfy at least one of the following Formula (4X) or (5X):

$1<$ an elastic modulus of the knee anterior surface part$(A)$/an elastic modulus of the femoral side anterior surface part$(C)$; and     Formula (4X):

$1<$ an elastic modulus of the knee anterior surface part$(A)$/an elastic modulus of the tibial side anterior surface part$(E)$.     Formula (5X):

3. The knee supporter according to claim 2, wherein the elastic moduli in the axial direction of the knee anterior surface part (A), the femoral side anterior surface part (C), and the tibial side anterior surface part (E), when stretched by 80% in the axial direction of the tubular supporter main body, satisfy both Formulas (4X) and (5X).

4. The knee supporter according to claim 1, wherein the elastic moduli in the axial direction of the knee anterior surface part (A), the femoral side anterior surface part (C), and the tibial side anterior surface part (E), when stretched by 80% in the axial direction of the tubular supporter main body, satisfy at least one of the following Formula (4Xa) or (5Xa):

$1<$ an elastic modulus of the knee anterior surface part$(A)$/an elastic modulus of the femoral side anterior surface part$(C)\leq 5$; and     Formula (4Xa):

$1<$ an elastic modulus of the knee anterior surface part$(A)$/an elastic modulus of the tibial side anterior surface part$(E)\leq 5$.     Formula (5Xa):

5. The knee supporter according to claim 1, wherein the elastic moduli in the axial direction of the knee anterior surface part (A), the femoral side anterior surface part (C), and the tibial side anterior surface part (E), when stretched by 80% in the axial direction of the tubular supporter main body, satisfy at least one of the following Formula (4Y) or (5Y):

$0.2\leq$ an elastic modulus of the knee anterior surface part$(A)$/an elastic modulus of the femoral side anterior surface part$(C)\leq 1$; and     Formula (4Y):

$0.2\leq$ an elastic modulus of the knee anterior surface part$(A)$/an elastic modulus of the tibial side anterior surface part$(E)\leq 1$.     Formula (5Y):

6. The knee supporter according to claim 5, wherein the elastic moduli in the axial direction of the knee anterior surface part (A), the femoral side anterior surface part (C), and the tibial side anterior surface part (E), when stretched by 80% in the axial direction of the tubular supporter main body, satisfy both Formulas (4Y) and (5Y).

7. The knee supporter according to claim 1, wherein the elastic moduli in the axial direction of the femoral side anterior surface part (C), the femoral side posterior surface part (D), the tibial side anterior surface part (E), and the tibial side posterior surface part (F), when stretched by 80% in the axial direction of the tubular supporter main body, satisfy at least one of the following Formula (6) or (7):

$1<$ an elastic modulus of the tibial side anterior surface part$(E)$/an elastic modulus of the femoral side posterior surface part$(D)$; and     Formula (6):

$1<$ an elastic modulus of the femoral side anterior surface part$(C)$/an elastic modulus of the tibial side posterior surface part$(F)$.     Formula (7):

8. The knee supporter according to claim 1, wherein the elastic moduli in the axial direction of the knee posterior surface part (B), the femoral side posterior surface part (D), and the tibial side posterior surface part (F), when stretched by 80% in the axial direction of the tubular supporter main body, satisfy at least one of the following Formula (8) or (9):

$$6 \leq \text{an elastic modulus of the knee posterior surface part}(B)/\text{an elastic modulus of the femoral side posterior surface part}(D) \leq 50; \text{ and} \quad \text{Formula (8)}$$

$$6 \leq \text{an elastic modulus of the knee posterior surface part}(B)/\text{an elastic modulus of the tibial side posterior surface part}(F) \leq 50. \quad \text{Formula (9)}$$

9. The knee supporter according to claim 1, wherein the elastic moduli in the axial direction of the femoral side anterior surface part (C), the femoral side posterior surface part (D), the tibial side anterior surface part (E), and the tibial side posterior surface part (F), when stretched by 80% in the axial direction of the tubular supporter main body, satisfy at least one of the following Formula (2a) or (3a):

$$2 \leq \text{an elastic modulus of the femoral side anterior surface part}(C)/\text{an elastic modulus of the femoral side posterior surface part}(D) \leq 40; \text{ and} \quad \text{Formula (2a)}$$

$$2 \leq \text{an elastic modulus of the tibial side anterior surface part}(E)/\text{an elastic modulus of the tibial side posterior surface part}(F) \leq 40. \quad \text{Formula (3a)}$$

10. The knee supporter according to claim 1, wherein the elastic moduli in the axial direction of the knee anterior surface part (A) and the knee posterior surface part (B), when stretched by 80% in the axial direction of the tubular supporter main body, satisfy the following Formula (1a):

$$1 < \text{an elastic modulus of the knee posterior surface part}(B)/\text{an elastic modulus of the knee anterior surface part}(A) \leq 3. \quad \text{Formula (1a)}$$

11. The knee supporter according to claim 1, wherein the elastic modulus in the axial direction of each of the femoral side posterior surface part (D) and the tibial side posterior surface part (F), when stretched by 80% in the axial direction of the tubular supporter main body, is 0.001 MPa or more, and the elastic modulus in the axial direction of the knee posterior surface part (B), when stretched by 80% in the axial direction of the tubular supporter main body, is 1.0 MPa or less.

12. The knee supporter according to claim 1, wherein each of a knit structure of the knee anterior surface part (A), a knit structure of the knee posterior surface part (B), a knit structure of the femoral side anterior surface part (C), a knit structure of the femoral side posterior surface part (D), a knit structure of the tibial side anterior surface part (E), and a knit structure of the tibial side posterior surface part (F), includes a float stitch structure.

13. The knee supporter according to claim 1, wherein a stretch rate in the axial direction of the knee anterior surface part (A), when stretched in the axial direction of the tubular supporter main body at a load of 20 N, is from 50% to 500%.

14. The knee supporter according to claim 1, wherein a stretch rate in the axial direction of each of the femoral side posterior surface part (D) and the tibial side posterior surface part (F), when stretched in the axial direction of the tubular supporter main body at a load of 20 N, is from 150% to 850%.

15. The knee supporter according to claim 1, wherein the tubular supporter main body is continuously manufactured by circular knitting.

16. The knee supporter according to claim 1, wherein the tubular supporter main body has a seamless structure.

17. The knee supporter according to claim 1, further comprising a femoral side rib top part disposed on a femoral side of the tubular supporter main body, and a tibial side rib top part disposed on a tibial side of the tubular supporter main body.

18. The knee supporter according to claim 1, wherein a ratio of the elastic modulus of the knee posterior surface part (B)/the elastic modulus of the knee anterior surface part (A) in Formula (1) is 1.1 or higher.

19. A garment, comprising the knee supporter according to claim 1.

* * * * *